(12) United States Patent
Tassoni, Jr. et al.

(10) Patent No.: US 11,351,048 B2
(45) Date of Patent: Jun. 7, 2022

(54) STENT DELIVERY SYSTEMS WITH A REINFORCED DEPLOYMENT SHEATH

(71) Applicant: BOSTON SCIENTIFIC SCIMED, INC., Maple Grove, MN (US)

(72) Inventors: Anthony F. Tassoni, Jr., Ramsey, MN (US); Mahfuza Ahmed, Brookline, MA (US); Nicholas L. Tassoni, Andover, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 514 days.

(21) Appl. No.: 15/351,957

(22) Filed: Nov. 15, 2016

(65) Prior Publication Data

US 2017/0135834 A1 May 18, 2017

Related U.S. Application Data

(60) Provisional application No. 62/255,837, filed on Nov. 16, 2015.

(51) Int. Cl.
*A61F 2/82* (2013.01)
*A61F 2/966* (2013.01)

(52) U.S. Cl.
CPC ...... *A61F 2/966* (2013.01); *A61F 2210/0014* (2013.01); *A61F 2210/0076* (2013.01); *A61F 2240/001* (2013.01); *A61F 2250/0091* (2013.01)

(58) Field of Classification Search
CPC ............... A61M 25/0012; A61F 2/966; A61F 2210/0076; A61F 2210/0014; A61F 2240/001; A61F 2/95
See application file for complete search history.

(56) References Cited

U.S. PATENT DOCUMENTS

| | | | |
|---|---|---|---|
| 1,553,227 | A | 9/1925 | Feyk et al. |
| 1,866,888 | A | 7/1932 | Hawley |
| 2,275,827 | A | 3/1942 | Plensler |
| 2,413,805 | A | 1/1947 | Vickers |
| 2,441,166 | A | 5/1948 | Raspet |
| 2,561,890 | A | 7/1951 | Stoddard |
| 2,722,614 | A | 11/1955 | Fryklund |
| 2,857,536 | A | 10/1958 | Light |
| 2,864,017 | A | 12/1958 | Waltscheff |
| 2,871,793 | A | 2/1959 | Michie et al. |
| 3,249,776 | A | 5/1966 | Anderson et al. |
| 3,322,984 | A | 5/1967 | Anderson |
| 3,334,523 | A | 8/1967 | Rieser |

(Continued)

FOREIGN PATENT DOCUMENTS

| | | |
|---|---|---|
| AU | 723040 B2 | 12/1997 |
| AU | 733966 B2 | 4/1998 |

(Continued)

*Primary Examiner* — Erich G Herbermann
(74) *Attorney, Agent, or Firm* — Seager, Tufte & Wickhem, LLP

(57) ABSTRACT

Stent delivery systems and methods for making and using the same are disclosed. An example stent delivery system may include an inner member. A deployment sheath may be disposed about the inner member. A stent may be disposed between the inner member and the deployment sheath. The deployment sheath may include a translucent reinforcing member that allows for visualization of the stent during stent deployment.

17 Claims, 9 Drawing Sheets

(56) References Cited

U.S. PATENT DOCUMENTS

| | | |
|---|---|---|
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,613,684 A | 10/1971 | Sheridan |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Willson |
| 4,318,402 A | 3/1982 | Vaillancourt |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,547,192 A | 10/1985 | Brodsky et al. |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gurs |
| 4,665,906 A | 5/1987 | Jervis |
| 4,665,918 A | 5/1987 | Garza et al. |
| 4,721,117 A | 1/1988 | Mar et al. |
| 4,732,152 A | 3/1988 | Wallsten et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa et al. |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,906,232 A | 3/1990 | Reynolds |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | De Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,026,377 A | 6/1991 | Burton et al. |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Towne et al. |
| 5,063,935 A | 11/1991 | Gambale |
| 5,071,407 A | 12/1991 | Termin et al. |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,158,548 A | 10/1992 | Lau et al. |
| 5,163,905 A | 11/1992 | Don Michael |
| 5,181,668 A | 1/1993 | Tsuji et al. |
| 5,195,984 A | 3/1993 | Schatz |
| 5,201,757 A | 4/1993 | Heyn et al. |
| 5,205,830 A | 4/1993 | Dassa et al. |
| 5,211,183 A | 5/1993 | Wilson |
| 5,221,261 A | 6/1993 | Termin et al. |
| 5,228,441 A | 7/1993 | Lundquist |
| 5,234,416 A | 8/1993 | Macaulay et al. |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,346,471 A | 9/1994 | Raulerson |
| 5,358,493 A | 10/1994 | Schweich, Jr. et al. |
| 5,365,942 A | 11/1994 | Shank |
| 5,365,943 A | 11/1994 | Jansen |
| 5,368,564 A | 11/1994 | Savage |
| 5,376,084 A | 12/1994 | Bacich et al. |
| 5,378,239 A | 1/1995 | Termin et al. |
| 5,381,782 A | 1/1995 | DeLaRama et al. |
| 5,406,960 A | 4/1995 | Corso, Jr. |
| 5,411,476 A | 5/1995 | Abrams et al. |
| 5,433,723 A | 7/1995 | Lindenberg et al. |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,443,907 A | 8/1995 | Slaikeu et al. |
| 5,445,646 A | 8/1995 | Euteneuer et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A | 12/1995 | Lundquist |
| 5,480,382 A | 1/1996 | Hammerslag et al. |
| 5,496,277 A | 3/1996 | Termin et al. |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |

(56) References Cited

U.S. PATENT DOCUMENTS

| | | |
|---|---|---|
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,534,007 A | 7/1996 | St. Germain et al. |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,571,135 A | 11/1996 | Fraser et al. |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirazee et al. |
| 5,622,184 A | 4/1997 | Ashby et al. |
| 5,630,806 A | 5/1997 | Inagaki et al. |
| 5,637,089 A | 6/1997 | Abrams et al. |
| 5,656,011 A | 8/1997 | Uihlein et al. |
| 5,658,264 A | 8/1997 | Samson |
| 5,662,703 A | 9/1997 | Yurek et al. |
| 5,666,968 A | 9/1997 | Imran et al. |
| 5,666,969 A | 9/1997 | Urick et al. |
| 5,669,926 A | 9/1997 | Aust et al. |
| 5,674,242 A | 10/1997 | Phan et al. |
| 5,676,659 A | 10/1997 | McGurk |
| 5,676,697 A | 10/1997 | McDonald |
| 5,682,894 A | 11/1997 | Orr et al. |
| 5,690,120 A | 11/1997 | Jacobsen et al. |
| 5,690,644 A | 11/1997 | Yurek et al. |
| 5,695,499 A | 12/1997 | Helgerson et al. |
| 5,702,364 A | 12/1997 | Euteneuer et al. |
| 5,702,373 A | 12/1997 | Samson |
| 5,713,860 A | 2/1998 | Kaplan et al. |
| 5,720,300 A | 2/1998 | Fagan et al. |
| 5,722,609 A | 3/1998 | Murakami |
| 5,728,063 A | 3/1998 | Preissman et al. |
| 5,733,267 A | 3/1998 | Del Toro |
| 5,741,429 A | 4/1998 | Donadio, III et al. |
| 5,746,701 A | 5/1998 | Noone |
| 5,755,777 A | 5/1998 | Chuter |
| 5,769,830 A | 6/1998 | Parker |
| 5,772,609 A | 6/1998 | Nguyen et al. |
| 5,772,669 A | 6/1998 | Vrba |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,827,225 A | 10/1998 | Schwab |
| 5,827,242 A | 10/1998 | Follmer et al. |
| 5,830,181 A | 11/1998 | Thornton |
| 5,833,632 A | 11/1998 | Jacobsen et al. |
| 5,833,694 A | 11/1998 | Poncet |
| 5,833,706 A | 11/1998 | St. Germain et al. |
| 5,836,923 A | 11/1998 | Mayer |
| 5,836,926 A | 11/1998 | Peterson et al. |
| 5,843,050 A | 12/1998 | Jones et al. |
| 5,843,090 A | 12/1998 | Schuetz |
| 5,843,091 A | 12/1998 | Holsinger et al. |
| 5,843,244 A | 12/1998 | Pelton et al. |
| 5,851,203 A | 12/1998 | van Muiden |
| 5,882,347 A | 3/1999 | Mouris-Laan et al. |
| 5,891,154 A | 4/1999 | Loeffler |
| 5,895,378 A | 4/1999 | Nita |
| 5,897,537 A | 4/1999 | Berg et al. |
| 5,902,254 A | 5/1999 | Magram |
| 5,902,290 A | 5/1999 | Peacock, III et al. |
| 5,904,657 A | 5/1999 | Unsworth et al. |
| 5,906,618 A | 5/1999 | Larson, III |
| 5,906,619 A | 5/1999 | Olson et al. |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noon et al. |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,954,764 A | 9/1999 | Parodi |
| 5,957,930 A | 9/1999 | Vrba |
| 5,971,975 A | 10/1999 | Mills et al. |
| 5,980,483 A | 11/1999 | Dimitri |
| 6,001,068 A | 12/1999 | Uchino et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,017,577 A | 1/2000 | Hostettler et al. |
| 6,019,778 A | 2/2000 | Wilson et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,033,413 A | 3/2000 | Mikus et al. |
| 6,042,553 A | 3/2000 | Solar et al. |
| 6,045,547 A | 4/2000 | Ren et al. |
| 6,048,339 A | 4/2000 | Zirps et al. |
| 6,056,702 A | 5/2000 | Lorenzo |
| 6,059,813 A | 5/2000 | Vrba et al. |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,106,485 A | 8/2000 | McMahon |
| 6,106,488 A | 8/2000 | Fleming et al. |
| 6,117,140 A | 9/2000 | Munsinger |
| 6,120,522 A | 9/2000 | Vrba et al. |
| 6,123,723 A | 9/2000 | Konya et al. |
| 6,139,510 A | 10/2000 | Palermo |
| 6,139,524 A | 10/2000 | Killion |
| 6,165,292 A | 12/2000 | Abrams et al. |
| 6,171,296 B1 | 1/2001 | Chow |
| 6,176,849 B1 | 1/2001 | Yang et al. |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| 6,206,888 B1 | 3/2001 | Bicek et al. |
| 6,214,042 B1 | 4/2001 | Jacobsen et al. |
| 6,221,467 B1 | 4/2001 | Nazarova et al. |
| 6,228,073 B1 | 5/2001 | Noone et al. |
| 6,238,410 B1 | 5/2001 | Vrba et al. |
| 6,248,082 B1 | 6/2001 | Jafari |
| 6,251,092 B1 | 6/2001 | Qin et al. |
| 6,254,549 B1 | 7/2001 | Ramzipoor |
| 6,254,609 B1 | 7/2001 | Vrba et al. |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,287,329 B1 | 9/2001 | Duerig et al. |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,322,586 B1 | 11/2001 | Monroe et al. |
| 6,325,790 B1 | 12/2001 | Trotta et al. |
| 6,330,884 B1 | 12/2001 | Kim |
| 6,331,184 B1 | 12/2001 | Abrams |
| 6,338,725 B1 | 1/2002 | Hermann et al. |
| 6,342,066 B1 | 1/2002 | Toro et al. |
| 6,346,091 B1 | 2/2002 | Jacobsen et al. |

(56) References Cited

U.S. PATENT DOCUMENTS

| | | |
|---|---|---|
| 6,352,515 B1 | 3/2002 | Anderson et al. |
| 6,355,005 B1 | 3/2002 | Powell et al. |
| 6,355,027 B1 | 3/2002 | Le et al. |
| 6,355,060 B1 | 3/2002 | Lenker et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,676 B1 | 4/2002 | Cox |
| 6,375,774 B1 | 4/2002 | Lunn et al. |
| 6,379,365 B1 | 4/2002 | Diaz |
| 6,379,369 B1 | 4/2002 | Abrams et al. |
| 6,380,457 B1 | 4/2002 | Yurek et al. |
| 6,390,993 B1 | 5/2002 | Cornish et al. |
| 6,391,050 B1 | 5/2002 | Broome |
| 6,398,758 B1 | 6/2002 | Jacobsen et al. |
| 6,398,802 B1 | 6/2002 | Yee |
| 6,425,898 B1 | 7/2002 | Wilson et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen et al. |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,503,244 B2 | 1/2003 | Hayman |
| 6,508,803 B1 | 1/2003 | Horikawa et al. |
| 6,514,228 B1 | 2/2003 | Hamilton et al. |
| 6,514,261 B1 | 2/2003 | Randall et al. |
| 6,524,301 B1 | 2/2003 | Wilson et al. |
| 6,530,934 B1 | 3/2003 | Jacobsen et al. |
| 6,544,278 B1 | 4/2003 | Vrba et al. |
| 6,547,779 B2 | 4/2003 | Levine et al. |
| 6,553,880 B2 | 4/2003 | Jacobsen et al. |
| 6,556,873 B1 | 4/2003 | Smits |
| 6,576,006 B2 | 6/2003 | Limon et al. |
| 6,579,246 B2 | 6/2003 | Jacobsen et al. |
| 6,589,251 B2 | 7/2003 | Yee et al. |
| 6,602,226 B1 | 8/2003 | Smith et al. |
| 6,602,280 B2 | 8/2003 | Chobotov |
| 6,610,046 B1 | 8/2003 | Usami et al. |
| 6,613,014 B1 | 9/2003 | Chi |
| 6,623,448 B2 | 9/2003 | Slater |
| 6,626,934 B2 | 9/2003 | Blaeser et al. |
| 6,636,758 B2 | 10/2003 | Sanchez et al. |
| 6,638,266 B2 | 10/2003 | Wilson et al. |
| 6,652,508 B2 | 11/2003 | Griffin et al. |
| 6,669,716 B1 | 12/2003 | Gilson et al. |
| 6,682,493 B2 | 1/2004 | Mirigian |
| 6,712,826 B2 | 3/2004 | Lui |
| 6,726,712 B1 | 4/2004 | Raeder-Devens et al. |
| 6,726,714 B2 | 4/2004 | DiCaprio et al. |
| 6,730,095 B2 | 5/2004 | Olson, Jr. et al. |
| 6,736,839 B2 | 5/2004 | Cummings |
| 6,749,560 B1 | 6/2004 | Konstorum et al. |
| 6,749,627 B2 | 6/2004 | Thompson et al. |
| 6,755,855 B2 | 6/2004 | Yurek et al. |
| 6,766,720 B1 | 7/2004 | Jacobsen et al. |
| 6,773,446 B1 | 8/2004 | Dwyer et al. |
| 6,776,791 B1 | 8/2004 | Stallings et al. |
| 6,777,644 B2 | 8/2004 | Peacock, III et al. |
| 6,802,849 B2 | 10/2004 | Blaeser et al. |
| 6,811,544 B2 | 11/2004 | Schaer |
| 6,837,898 B2 | 1/2005 | Boyle et al. |
| 6,860,898 B2 | 3/2005 | Stack et al. |
| 6,866,642 B2 | 3/2005 | Kellerman et al. |
| 6,887,235 B2 | 5/2005 | O'Connor et al. |
| 6,918,882 B2 | 7/2005 | Skujins et al. |
| 6,939,352 B2 | 9/2005 | Buzzard et al. |
| 6,942,682 B2 | 9/2005 | Vrba et al. |
| 6,951,675 B2 | 10/2005 | Chin et al. |
| 6,997,937 B2 | 2/2006 | Jacobsen et al. |
| 7,001,369 B2 | 2/2006 | Griffin et al. |
| 7,001,423 B2 | 2/2006 | Euteneuer et al. |
| 7,074,197 B2 | 7/2006 | Reynolds et al. |
| 7,278,998 B2 | 10/2007 | Gaschino et al. |
| 7,387,640 B2 | 6/2008 | Cummings |
| 7,540,865 B2 | 6/2009 | Griffin et al. |
| 7,632,296 B2 | 12/2009 | Malewicz |
| 7,740,652 B2 | 6/2010 | Gerdts et al. |
| 7,914,466 B2 | 3/2011 | Davis et al. |
| 7,955,272 B2 | 6/2011 | Rooney et al. |
| 8,048,004 B2 | 11/2011 | Davis et al. |
| 8,048,060 B2 | 11/2011 | Griffin et al. |
| 8,128,676 B2 | 3/2012 | Cummings |
| 8,152,818 B2 | 4/2012 | Gunderson |
| 8,182,465 B2 | 5/2012 | Griffin et al. |
| 8,753,328 B2 * | 6/2014 | Aherne ............... A61M 25/005 604/527 |
| 8,784,468 B2 | 7/2014 | Gerdts et al. |
| 8,858,530 B2 * | 10/2014 | Nishigishi ......... A61M 25/0053 138/123 |
| 9,084,692 B2 | 7/2015 | Hacker et al. |
| 2001/0034548 A1 | 10/2001 | Vrba et al. |
| 2001/0034549 A1 | 10/2001 | Bartholf et al. |
| 2001/0037141 A1 | 11/2001 | Yee et al. |
| 2002/0013540 A1 | 1/2002 | Jacobsen et al. |
| 2002/0019599 A1 | 2/2002 | Rooney et al. |
| 2002/0052641 A1 | 5/2002 | Monroe et al. |
| 2002/0058951 A1 | 5/2002 | Fiedler |
| 2002/0082550 A1 | 6/2002 | Hamilton et al. |
| 2002/0095203 A1 | 7/2002 | Thompson et al. |
| 2002/0103525 A1 | 8/2002 | Cummings |
| 2002/0165523 A1 | 11/2002 | Chin et al. |
| 2003/0009208 A1 | 1/2003 | Snyder et al. |
| 2003/0060732 A1 | 3/2003 | Jacobsen et al. |
| 2003/0069520 A1 | 4/2003 | Skujins et al. |
| 2003/0069521 A1 | 4/2003 | Reynolds et al. |
| 2003/0069522 A1 | 4/2003 | Jacobsen et al. |
| 2003/0139759 A1 * | 7/2003 | Schaible ............... A61M 25/00 606/194 |
| 2003/0163156 A1 | 8/2003 | Hebert et al. |
| 2004/0098083 A1 | 5/2004 | Tran et al. |
| 2004/0148009 A1 | 7/2004 | Buzzard et al. |
| 2004/0167437 A1 | 8/2004 | Sharrow et al. |
| 2004/0181174 A2 | 9/2004 | Davis et al. |
| 2004/0181176 A1 | 9/2004 | Jafar et al. |
| 2004/0215317 A1 | 10/2004 | Cummings |
| 2004/0267348 A1 | 12/2004 | Gunderson et al. |
| 2005/0027345 A1 | 2/2005 | Horan et al. |
| 2005/0080476 A1 | 4/2005 | Gunderson et al. |
| 2005/0149159 A1 | 7/2005 | Andreas et al. |
| 2005/0154439 A1 | 7/2005 | Gunderson |
| 2005/0182475 A1 | 8/2005 | Jen et al. |
| 2005/0192657 A1 | 9/2005 | Colen et al. |
| 2005/0240254 A1 | 10/2005 | Austin |
| 2005/0256562 A1 | 11/2005 | Clerc et al. |
| 2006/0009833 A1 | 1/2006 | Chobotov et al. |
| 2006/0030923 A1 | 2/2006 | Gunderson |
| 2006/0041302 A1 | 2/2006 | Malewicz |
| 2006/0074477 A1 | 4/2006 | Berthiaume et al. |
| 2006/0189896 A1 | 8/2006 | Davis et al. |
| 2006/0190069 A1 | 8/2006 | Baker-Janis et al. |
| 2006/0229697 A1 | 10/2006 | Gerdts et al. |
| 2006/0264904 A1 | 11/2006 | Kerby et al. |
| 2006/0292300 A1 | 12/2006 | Tan |
| 2007/0142894 A1 | 6/2007 | Moore et al. |
| 2007/0208350 A1 | 9/2007 | Gunderson |
| 2007/0282420 A1 | 12/2007 | Gunderson |
| 2008/0021347 A1 | 1/2008 | Jacobsen et al. |
| 2008/0021348 A1 | 1/2008 | Jacobsen et al. |
| 2008/0021400 A1 | 1/2008 | Jacobsen et al. |
| 2008/0021401 A1 | 1/2008 | Jacobsen et al. |
| 2008/0021402 A1 | 1/2008 | Jacobsen et al. |
| 2008/0021403 A1 | 1/2008 | Jacobsen et al. |
| 2008/0021405 A1 | 1/2008 | Jacobsen et al. |
| 2008/0021406 A1 | 1/2008 | Jacobsen et al. |
| 2008/0021407 A1 | 1/2008 | Jacobsen et al. |
| 2008/0021408 A1 | 1/2008 | Jacobsen et al. |
| 2008/0077119 A1 | 3/2008 | Snyder et al. |
| 2008/0135752 A1 * | 6/2008 | Motoi ..................... G01N 1/32 250/309 |
| 2008/0188920 A1 | 8/2008 | Moberg et al. |
| 2009/0036967 A1 | 2/2009 | Cummings |

(56) References Cited

U.S. PATENT DOCUMENTS

| | | | |
|---|---|---|---|
| 2009/0048654 A1* | 2/2009 | Chmura | A61F 2/95 623/1.11 |
| 2009/0099637 A1 | 4/2009 | Barthold et al. | |
| 2009/0192584 A1 | 7/2009 | Gerdts et al. | |
| 2010/0256727 A1 | 10/2010 | Gerdts et al. | |
| 2013/0013047 A1 | 1/2013 | Ramos et al. | |
| 2014/0276412 A1* | 9/2014 | Shumer | A61M 25/0009 604/131 |
| 2015/0057639 A1 | 2/2015 | Storbeck et al. | |

FOREIGN PATENT DOCUMENTS

| | | |
|---|---|---|
| BR | 9712829 A | 1/2000 |
| CA | 2266685 C | 5/2006 |
| CN | 1230914 A | 10/1999 |
| DE | 2539191 A1 | 3/1976 |
| DE | 3621967 A1 | 1/1988 |
| EP | 0045931 A2 | 2/1982 |
| EP | 0069522 A1 | 1/1983 |
| EP | 0087933 A1 | 9/1983 |
| EP | 0111044 A2 | 6/1984 |
| EP | 0181174 A2 | 5/1986 |
| EP | 0377453 A1 | 7/1990 |
| EP | 0521595 A2 | 1/1993 |
| EP | 0565065 A1 | 10/1993 |
| EP | 0608853 A2 | 8/1994 |
| EP | 0676936 A1 | 10/1995 |
| EP | 0684022 A2 | 11/1995 |
| EP | 0775470 A1 | 5/1997 |
| EP | 0778038 A2 | 6/1997 |
| EP | 0778039 A1 | 6/1997 |
| EP | 0778040 A2 | 6/1997 |
| EP | 0790066 A2 | 8/1997 |
| EP | 0807446 A2 | 11/1997 |
| EP | 0812599 A2 | 12/1997 |
| EP | 0865772 A1 | 9/1998 |
| EP | 0865773 A1 | 9/1998 |
| EP | 0917885 A1 | 5/1999 |
| EP | 0937481 A1 | 8/1999 |
| EP | 0820259 B1 | 2/2003 |
| EP | 0935947 B1 | 12/2004 |
| EP | 0934141 B1 | 11/2005 |
| EP | 0385450 B1 | 3/2007 |
| GB | 2214354 A | 8/1989 |
| GB | 2257269 A | 1/1993 |
| JP | 588522 A | 1/1983 |
| JP | 60091858 A | 5/1985 |
| JP | 61022752 A | 1/1986 |
| JP | 62023361 A | 1/1987 |
| JP | 62089470 A | 4/1987 |
| JP | 63093516 A | 4/1988 |
| JP | 63181774 A | 7/1988 |
| JP | 3122850 U | 12/1991 |
| JP | 4061840 A | 2/1992 |
| JP | 4099963 A | 3/1992 |
| JP | 4213069 A | 8/1992 |
| JP | 4213070 A | 8/1992 |
| JP | 4236965 A | 8/1992 |
| JP | 5149969 A | 6/1993 |
| JP | 5506806 A | 10/1993 |
| JP | 5309519 A | 11/1993 |
| JP | 5507857 A | 11/1993 |
| JP | 6501179 A | 2/1994 |
| JP | 6169996 A | 6/1994 |
| JP | 6312313 A | 11/1994 |
| JP | 728562 U | 5/1995 |
| JP | 7124263 A | 5/1995 |
| JP | 7505561 A | 6/1995 |
| JP | 7037199 U | 7/1995 |
| JP | 7185009 A | 7/1995 |
| JP | 7275366 A | 10/1995 |
| JP | 751067 Y | 11/1995 |
| JP | 8229888 A | 9/1996 |
| JP | 8509141 A | 10/1996 |
| JP | 9294813 A | 11/1997 |
| JP | 10118193 A | 5/1998 |
| JP | 10305039 B2 | 11/1998 |
| JP | 10328191 A | 12/1998 |
| JP | 11226131 A | 8/1999 |
| JP | 11267224 A | 10/1999 |
| JP | 2000197704 A | 8/2000 |
| JP | 2000510722 A | 8/2000 |
| JP | 2000511083 A | 8/2000 |
| JP | 2001500808 A | 1/2001 |
| JP | 2002529137 A | 9/2002 |
| JP | 2002542901 A | 12/2002 |
| JP | 2002543896 A | 12/2002 |
| JP | 2003517893 A | 6/2003 |
| JP | 3649604 B2 | 2/2005 |
| JP | 2005534407 A | 11/2005 |
| SU | 1529365 A1 | 12/1989 |
| WO | 9002520 A1 | 3/1990 |
| WO | 9113364 A2 | 9/1991 |
| WO | 9204072 A1 | 3/1992 |
| WO | 9207619 A1 | 5/1992 |
| WO | 9304722 A2 | 3/1993 |
| WO | 9311313 A1 | 6/1993 |
| WO | 9524236 A1 | 9/1995 |
| WO | 9619255 A1 | 6/1996 |
| WO | 9710022 A2 | 3/1997 |
| WO | 9717899 A1 | 5/1997 |
| WO | 9725914 A1 | 7/1997 |
| WO | 9743949 A1 | 11/1997 |
| WO | 9744083 A1 | 11/1997 |
| WO | 9744086 A1 | 11/1997 |
| WO | 9810694 A3 | 3/1998 |
| WO | 9904847 A1 | 2/1999 |
| WO | 9911313 A1 | 3/1999 |
| WO | 9949808 A1 | 10/1999 |
| WO | 0018330 A1 | 4/2000 |
| WO | 0023139 A1 | 4/2000 |
| WO | 0027303 A2 | 5/2000 |
| WO | 0027309 A1 | 5/2000 |
| WO | 0030710 A1 | 6/2000 |
| WO | 0048645 A2 | 8/2000 |
| WO | 0057943 A1 | 10/2000 |
| WO | 0066199 A1 | 11/2000 |
| WO | 0067828 A1 | 11/2000 |
| WO | 0067845 A1 | 11/2000 |
| WO | 0071059 A1 | 11/2000 |
| WO | 0072907 A1 | 12/2000 |
| WO | 0128620 A1 | 4/2001 |
| WO | 0136034 A2 | 5/2001 |
| WO | 0145773 A1 | 6/2001 |
| WO | 0145912 A1 | 6/2001 |
| WO | 0176676 A2 | 10/2001 |
| WO | 0193920 A2 | 12/2001 |
| WO | 0213682 A1 | 2/2002 |
| WO | 02056953 A2 | 7/2002 |
| WO | 02062540 A2 | 8/2002 |
| WO | 03004086 A2 | 1/2003 |
| WO | 03008148 A2 | 1/2003 |
| WO | 2004012804 A2 | 2/2004 |
| WO | 2004047899 A1 | 6/2004 |
| WO | 2004098692 A1 | 11/2004 |
| WO | 2005020856 A2 | 3/2005 |
| WO | 2005107644 A1 | 11/2005 |
| WO | 2005112824 A1 | 12/2005 |
| WO | 2006036472 A1 | 4/2006 |
| WO | 2007084370 A1 | 7/2007 |
| WO | 2012116337 A1 | 8/2012 |

* cited by examiner

STENT DELIVERY SYSTEMS WITH A REINFORCED DEPLOYMENT SHEATH

CROSS-REFERENCE TO RELATED APPLICATIONS

This application claims priority under 35 U.S.C. § 119 to U.S. Provisional Application Ser. No. 62/255,837, filed Nov. 16, 2015, the entirety of which is incorporated herein by reference.

TECHNICAL FIELD

The present invention pertains to medical devices and methods for making and using medical devices. More particularly, the present invention pertains to stent delivery systems.

BACKGROUND

A wide variety of intracorporeal medical devices have been developed for medical use, for example, intravascular use. Some of these devices include stent delivery systems. These devices are manufactured by any one of a variety of different manufacturing methods and may be used according to any one of a variety of methods. Of the known stent delivery devices and methods for making and using the same, each has certain advantages and disadvantages. There is an ongoing need to provide alternative stent delivery devices as well as alternative methods for making and using stent delivery devices.

BRIEF SUMMARY

The disclosure provides design, material, manufacturing method, and use alternatives for stent delivery systems. An example stent delivery system is disclosed. The stent delivery system comprises:
an inner member;
a deployment sheath disposed about the inner member;
a stent disposed between the inner member and the deployment sheath; and
wherein the deployment sheath includes a translucent reinforcing member that allows for visualization of the stent during stent deployment.

Alternatively or additionally to any of the embodiments above, the stent includes a self-expanding stent.

Alternatively or additionally to any of the embodiments above, the translucent reinforcing member includes a braid.

Alternatively or additionally to any of the embodiments above, the translucent reinforcing member includes a coil.

Alternatively or additionally to any of the embodiments above, the translucent reinforcing member includes a polymer.

Alternatively or additionally to any of the embodiments above, the translucent reinforcing member includes polyetheretherketone.

Alternatively or additionally to any of the embodiments above, the deployment sheath has a length, and wherein the translucent reinforcing member extends along substantially the entire length of the deployment sheath.

Alternatively or additionally to any of the embodiments above, the deployment sheath has a proximal region and a distal region, and wherein the translucent reinforcing member extends along the distal region.

Alternatively or additionally to any of the embodiments above, the distal region has an enlarged outer diameter relative to the proximal region, an enlarged inner diameter relative to the proximal region, or both.

Alternatively or additionally to any of the embodiments above, the deployment sheath includes an inner liner and an outer layer, and wherein at least a portion of the translucent reinforcing member is disposed between the inner liner and the outer layer.

Alternatively or additionally to any of the embodiments above, the inner liner, the outer layer, or both are at least partially translucent.

Alternatively or additionally to any of the embodiments above, further comprising a handle coupled to the inner member and to the deployment sheath, the handle including an actuation member capable of shifting the longitudinal position of the deployment sheath relative to the inner member.

A method for manufacturing a stent delivery system is disclosed. The method comprises:
forming a deployment sheath, wherein forming the deployment sheath comprises:
positioning an inner liner along a mandrel,
disposing a translucent reinforcing member along the inner liner, and
disposing an outer layer along the translucent reinforcing member;
disposing an inner member within the deployment sheath; and
disposing a stent between the inner member and the deployment sheath.

Alternatively or additionally to any of the embodiments above, the translucent reinforcing member includes polyetheretherketone.

Alternatively or additionally to any of the embodiments above, the inner liner, the outer layer, or both are at least partially translucent.

A stent delivery system for use along a biliary tract, an enteral tract, or an airway is disclosed. The stent delivery system comprises:
an inner member;
a deployment sheath disposed about the inner member;
a self-expanding stent disposed between the inner member and the deployment sheath; and
wherein the deployment sheath includes an inner liner, an outer layer, and a translucent braided reinforcing member disposed at least partially between the inner liner and the outer layer, the translucent braided reinforcing member being capable of allowing for visualization of the self-expanding stent during stent deployment.

Alternatively or additionally to any of the embodiments above, the translucent braided reinforcing member includes a polymer.

Alternatively or additionally to any of the embodiments above, the translucent braided reinforcing member includes polyetheretherketone.

Alternatively or additionally to any of the embodiments above, the deployment sheath has a proximal region and a distal region, and wherein the translucent braided reinforcing member extends along at least the distal region.

Alternatively or additionally to any of the embodiments above, the distal region has an enlarged outer diameter relative to the proximal region, an enlarged inner diameter relative to the proximal region, or both.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
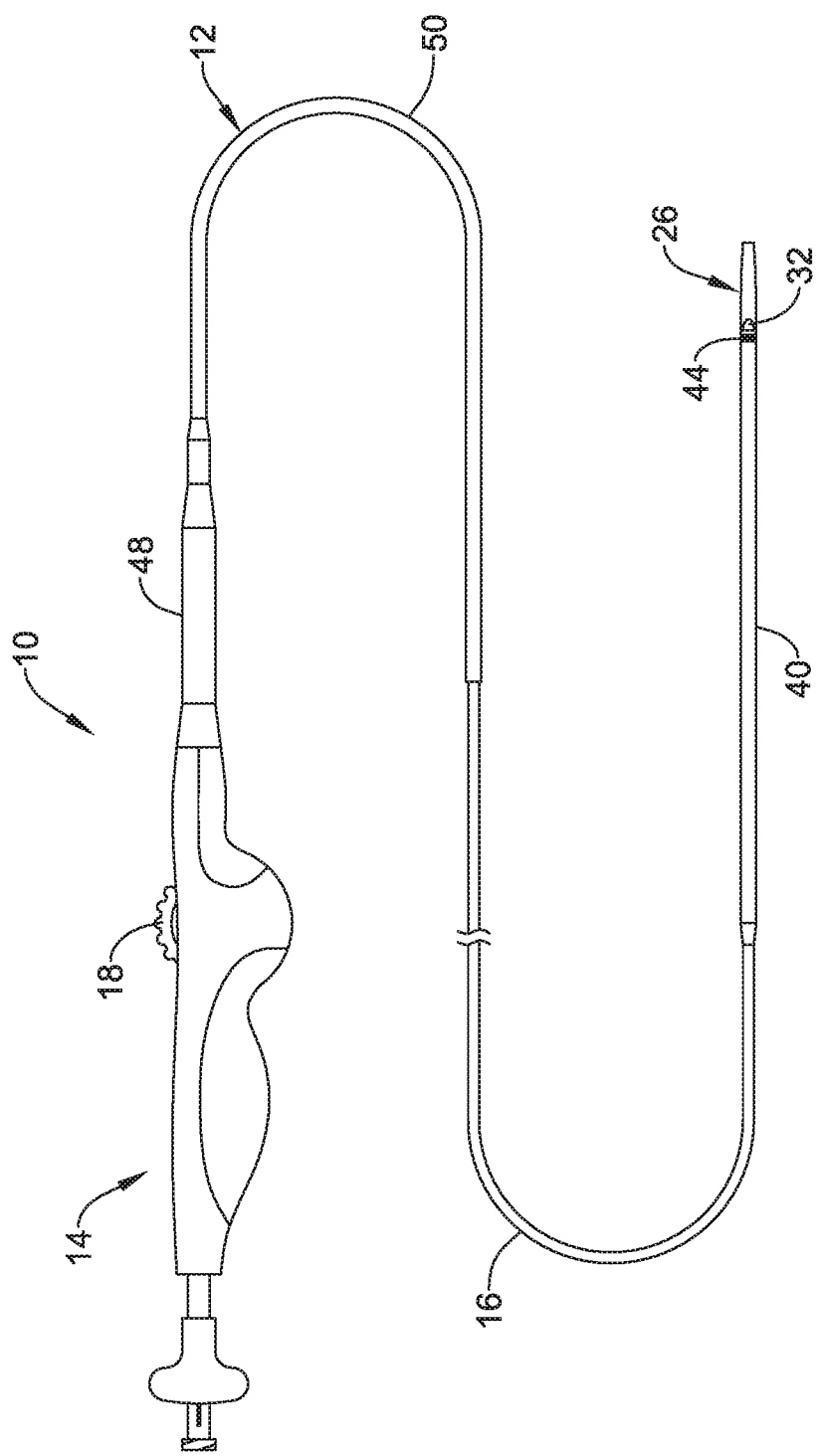
FIG. 1 is a partial cross-sectional side view of an example stent delivery system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates an example stent delivery system 10. System 10 may include an elongate shaft 12 and a handle 14 coupled to shaft 12. In general, system 10 may be used to deliver a suitable stent, graft, endoprosthesis or the like to an area of interest within a body lumen of a patient. In some instances, the body lumen may be a blood vessel located near the heart (e.g., within or near a cardiac vessel), within a peripheral vessel, within a neurological vessel, or at any other suitable location. In other instances, the body lumen may be along the biliary tract, enteral tract, along an airway, or the like. Deployment of the stent may include the proximal retraction of a retraction sheath 16, which overlies the stent. Retraction of sheath 16 may include the actuation of an actuation member 18 generally disposed at handle 14. In the example illustrated in FIG. 1, actuation member 18 is a thumbwheel that can be rotated by a clinician in order to accomplish proximal retraction of deployment sheath 16. Numerous other actuation members are contemplated. A number of other structures and features of system 10 can be seen in FIG. 1 and are labeled with reference numbers. Additional discussion of these structures can be found below.

Figure 2:
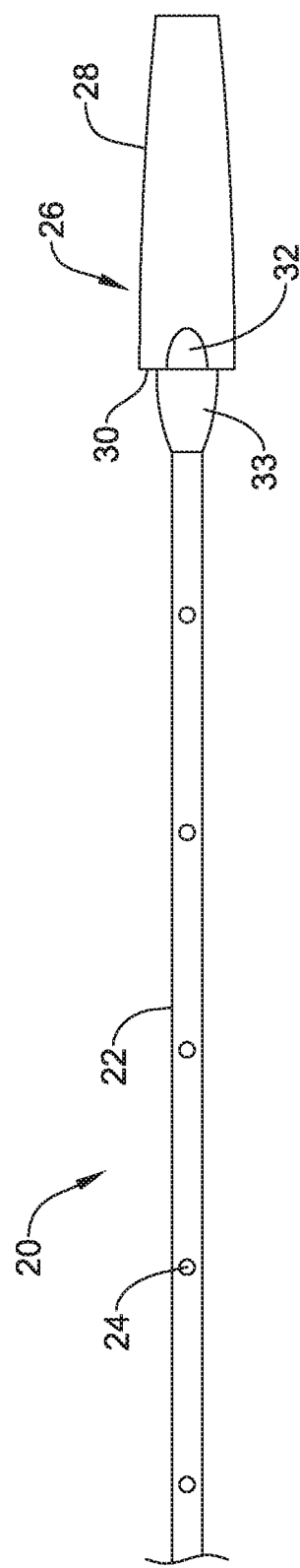
FIG. 2 is a side view of a portion of an example stent delivery system.
Figure 3:
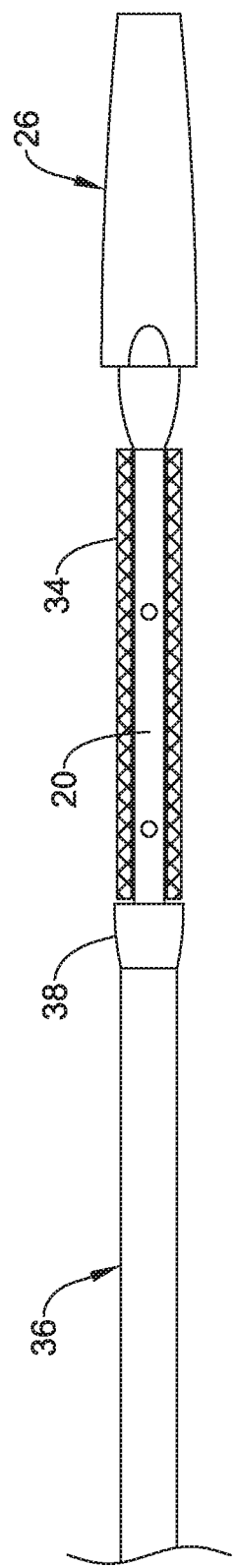
FIG. 3 is a side view of a portion of an example stent delivery system.
Figure 4:
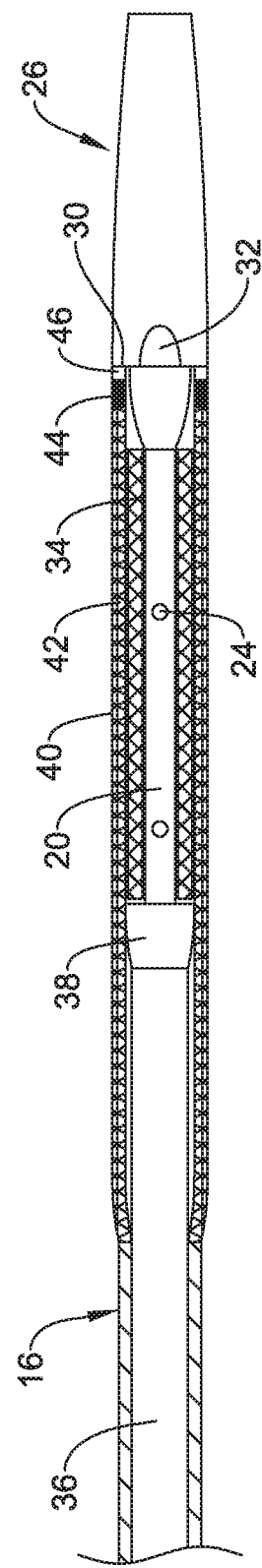
FIG. 4 is a side view of a portion of an example stent delivery system.

FIGS. 2-4 illustrate at least some of the structural components that may be included as a part of system 10. For example, system 10 may include an inner shaft or member 20 as illustrated in FIG. 2. In at least some embodiments, inner member 20 may be a tubular structure and, thus, may include a lumen (not shown). The lumen may be a guidewire lumen that extends along at least a portion of the length of inner member 20. Accordingly, system 10 may be advanced over a guidewire to the desired target location in the vasculature. In addition, or in alternative embodiments, the lumen may be a perfusion/aspiration lumen that allows portions, components, or all of system 10 to be flushed, perfused, aspirated, or the like.

Inner member 20 may include a stent receiving region 22 about which a stent (not shown, can be seen in FIGS. 3-4) may be disposed. The length and/or configuration of stent receiving region 22 may vary. For example, stent receiving region 22 may have a length sufficient for the stent to be disposed thereon. It can be appreciated that as the length of the stent utilized for system 10 increases, the length of stent receiving region 22 also increases.

Along or otherwise disposed adjacent stent receiving region 22 may be one or more perfusion ports 24. Ports 24 may extend through the wall of inner member 20 such that fluid may be infused through the lumen of inner member 20 and may be flushed through ports 24. This may be desirable for a number of reasons. For example, ports 24 may allow a clinician to evacuate air bubbles that may be trapped adjacent the stent by perfusing fluid through ports 24. In addition, ports 24 may be used to aspirate fluid that may be disposed along inner member 20. Ports 24 may also aid in sterilization and/or other preparatory processing steps that may be involved in preparing system 10 for use.

A tip 26 may be attached to or otherwise disposed at the distal end of inner member 20. Tip 26 may generally have a rounded or smooth shape that provides a generally atraumatic distal end to system 10. For example, tip 26 may have a smooth tapered distal portion 28 that gently tapers. Tip may also include a proximal ridge 30 that is configured so that sheath 16 can abut therewith. Tip 26 may also include a tapered proximal portion 33. Numerous other shapes and/or configurations are contemplated for tip 26.

Tip 26 may also include one or more cutouts or flats 32 formed therein. For the purposes of this disclosure, flats 32 are understood to be cutouts or flattened portions of tip 26 where the outer dimension or profile of tip 26 is reduced. The name "flats" comes from the fact that these regions may have a somewhat "flat" appearance when compared to the remainder of tip 26, which generally may have a rounded profile. The shape, however, of flats 32 is not meant to be limited to being flat or planar as numerous shapes are contemplated.

Flats 32 may allow for a gap or space to be defined between inner member 20 and deployment sheath 16 when sheath 16 abuts proximal ridge 30 of tip 26. This gap may allow for fluid, for example perfusion fluid passed through ports 24, to flow out from sheath 16. Thus, flats 32 may be used in conjunction with ports 24 to allow portions or all of system 10 to be flushed or otherwise evacuated of air bubbles.

FIG. 3 illustrates inner member 20 with some additional structure of system 10. In this figure, a stent 34 is disposed about inner member 20 (e.g., about stent receiving region 22 of inner member 20). In some embodiments, stent 34 is a self-expanding stent. Accordingly, stent 34 may be biased to outwardly expand. Because of this, stent 34 may not be "loaded onto" inner member 20 in a strict sense but rather may be thought of as being disposed about or surrounding inner member 20. Stent 34 may then be restrained within deployment sheath 16. In alternative embodiments, however, stent 34 may be directly loaded onto inner member 20 via crimping or any other suitable mechanical holding mechanism.

An intermediate tube 36 may also be disposed over inner member 20. In at least some embodiments, intermediate tube 36 may extend from a position adjacent to the proximal end of inner member 20 to a position proximal of the distal end of inner member 20. Intermediate tube 36 may include a bumper 38. In practice, bumper 38 may function by preventing any unwanted proximal movement of stent 38 during navigation and/or deployment of stent 38.

Bumper 38 may have any suitable form. In some embodiments, bumper 38 may be defined by a relatively short tube or sleeve that is disposed about intermediate tube 36. The material utilized for the sleeve may be the same or different from that of intermediate tube 36. Intermediate tube 36 may have a tapered or otherwise smooth transition in outer diameter adjacent bumper 38. For example, polymeric material may be disposed or reflowed adjacent bumper 38 (which may include disposing the polymeric material about a portion or all of bumper 38) so as to define a gentle transition in outer diameter at bumper 38. Other configurations are contemplated and may be utilized in alternative embodiments.

FIG. 4 illustrates additional structure of system 10. Here deployment sheath 16 can be seen disposed over inner member 20, intermediate tube 36, and stent 34. It can be appreciated that sheath 16 is configured to shift between a first position, for example as shown in FIG. 4, where sheath 16 overlies stent 34 and a second position where sheath 16 is proximally retracted to a position substantially proximal of stent 34. In general, the first position may be utilized during navigation of system 10 to the appropriate location within a body lumen and the second position may be used to deploy stent 34.

Sheath 16 may include a flared portion 40 where the outer diameter of sheath 16 is increased. In portion 40, the thickness of the tubular wall of sheath 16 may or may not be increased. Flared portion 40 may be desirable for a number of reasons. For example, flared portion 40 may allow sheath 16 to have an adequate inner dimension that is suitable so that sheath 16 may be disposed about stent 34 and bumper 38.

FIG. 4 also illustrates the distal end 46 of sheath 16 abutting proximal ridge 30. In this configuration, stent 34 can be flushed (e.g., to remove air bubbles) by infusing fluid through inner member 20 and through ports 24. Because of flats 32, fluid may be allowed to be flushed out of sheath 16 by passing through the gaps formed between inner member 20 and sheath 16 at flats 32.

Sheath 16 may also include a radiopaque marker or band 44. In general, marker band 44 may be disposed adjacent to the distal end 46 of sheath 16. One or more additional marker bands 44 may be disposed along other portions of sheath 16 or other portions of system 10. Marker band 44 may allow the distal end 46 of sheath 16 to be fluoroscopically visualized during advancement of system 10 and/or deployment of stent 34.

In at least some embodiments, sheath 16 may include a reinforcing member 42 embedded or otherwise included therewith. Reinforcing member 42 may have any number of a variety of different configurations. For example, reinforcing member 42 may include a braid, coil, mesh, combinations thereof, or the like, or any other suitable configuration. In some embodiments, reinforcing member 42 may extend along the entire length of sheath 16. In other embodiments, reinforcing member 42 may extend along one or more portions of the length of sheath 16. For example, reinforcing member 42 may extend along flared portion 40, along the distal portion of sheath, etc. In some instances, reinforcing member 42 may include a plurality of sections. For example, reinforcing member 42 may include a proximal section and a distal section. The proximal section and the distal section may be formed from the same materials or from different materials.

Figure 6:
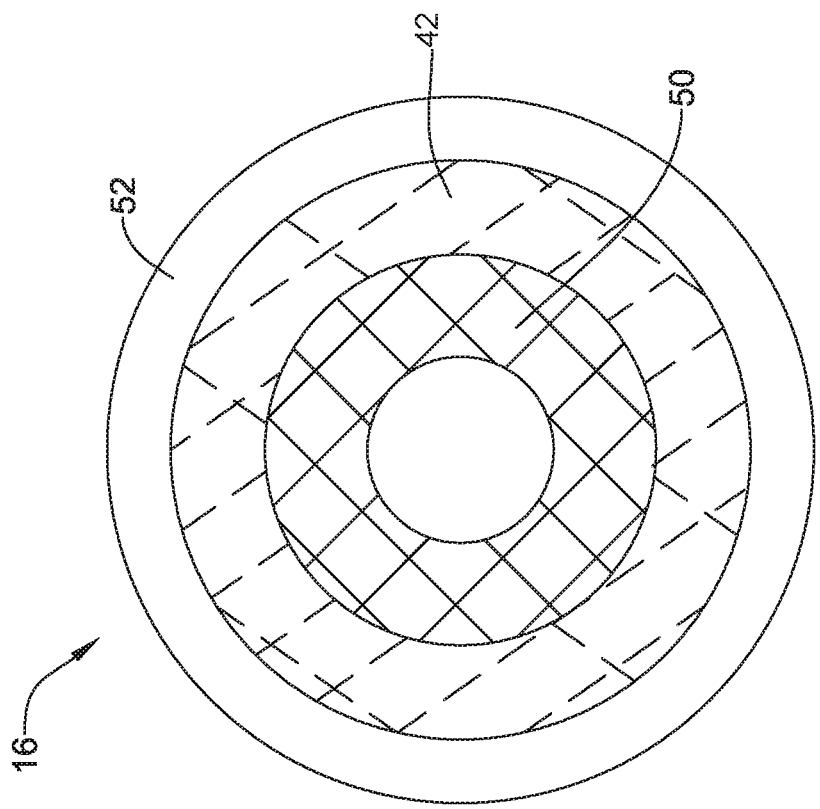
FIG. 6 is a cross-sectional view taken through line 6-6 in FIG. 5.

Sheath 16 is illustrated schematically in FIG. 6, with reinforcing member 42 shown in phantom line. Reinforcing member 42 may be formed from a suitable material such as those materials disclosed herein. In some instances, it may be desirable to visualize stent 34 through sheath 16 (and reinforcing member 42) prior to delivery and/or during delivery. Accordingly, reinforcing member 42 may be partially and/or substantially translucent, partially transparent, fully transparent, or otherwise sufficiently clear in order to allow a clinician to visualize stent 34 through reinforcing member 42. In some instances, reinforcing member 42 is formed from polyetheretherketone (PEEK). Other materials are contemplated including clear, translucent, or transparent materials. For example, reinforcing member 42 may include polyethylene terephthalate (PET), ultra-high molecular weight polyethylene (UHMWPE), or the like. In addition, sheath 16 may also be formed from material(s) that are partially and/or substantially translucent, partially transparent, fully transparent, or otherwise sufficiently clear in order to allow a clinician to visualize stent 34 therethrough.

Figure 5:
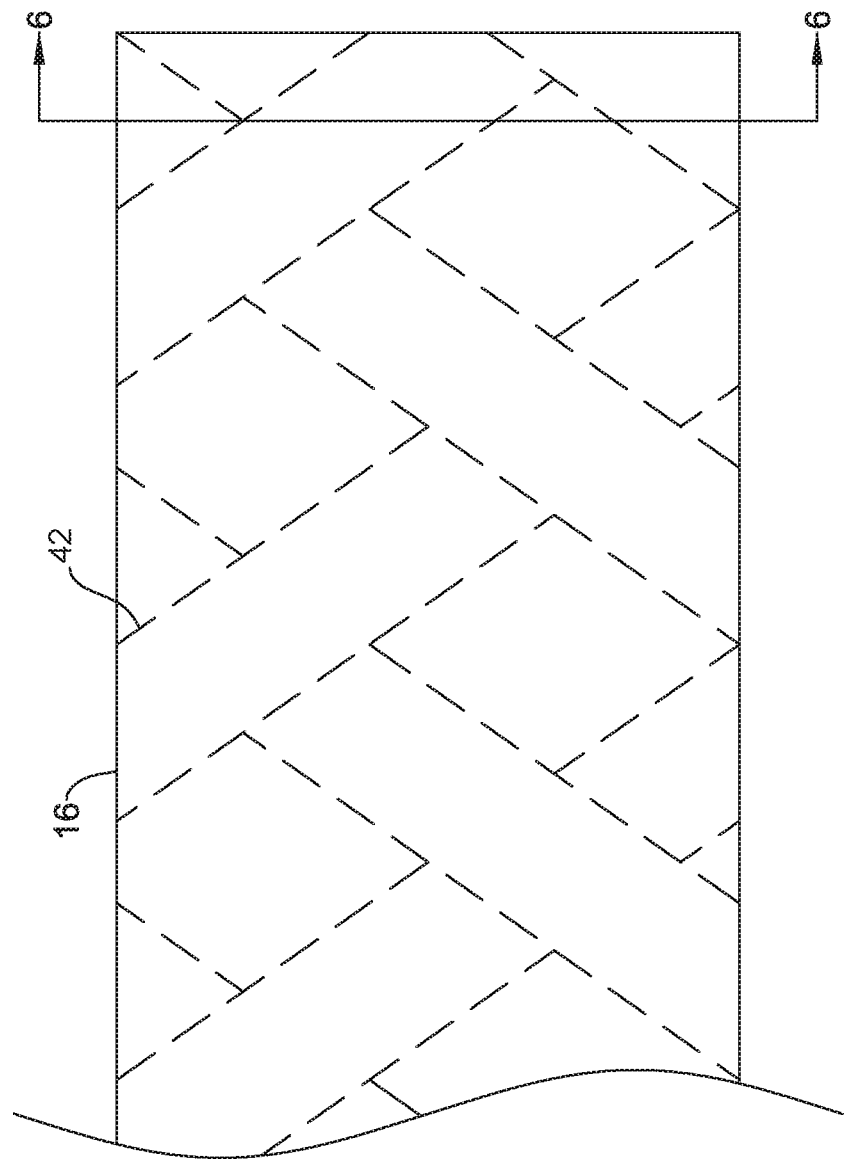
FIG. 5 is a side view of a portion of an example stent delivery system.

FIG. 6 is a cross-sectional view of sheath 16 taken through line 6-6 in FIG. 5. Here it can be seen that sheath 16 may include multiple layers. For example, sheath 16 may include an inner layer or liner 50 and an outer layer 52. Reinforcing member 42 may be at least partially disposed between inner liner 50 and outer layer 52. Inner liner 50, outer layer 52, or both may be formed from a suitable material. In at least some instances, inner liner 50, outer layer 52, or both may be formed from material(s) that are partially and/or substantially translucent, partially transparent, fully transparent, or otherwise sufficiently clear in order to allow a clinician to visualize stent 34 therethrough.

Figure 7:
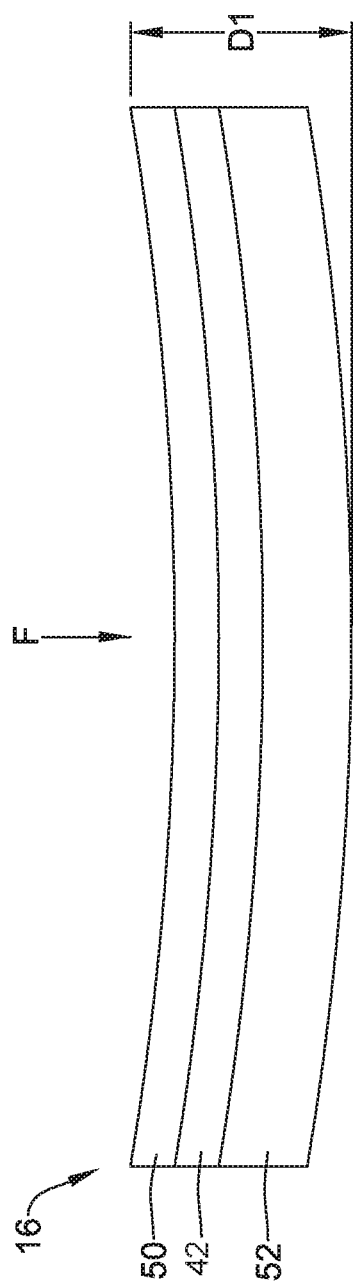
FIG. 7 is a schematic illustration of a portion of an example stent delivery system.
Figure 8:
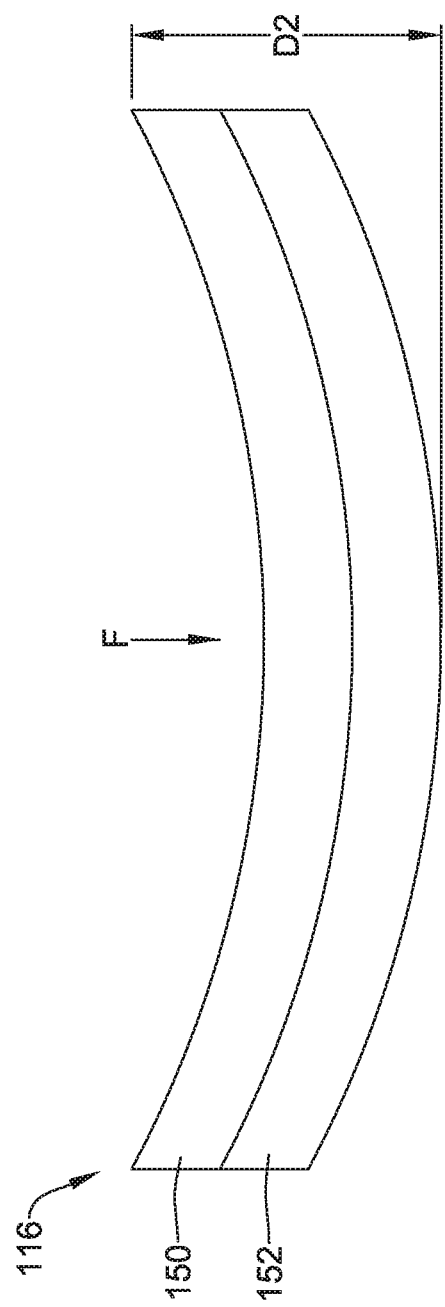
FIG. 8 is a schematic illustration of a portion of an example stent delivery system.

In addition to permitting visualization, sheath 16 may also provide other desirable features. For example, in some instances stent 34 may be a self-expanding stent. Self-expanding stents may have a tendency to exert an outward radial force when restrained, for example onto sheath 16. In some instances, the outward radial forces exerted on sheath could lead to the stent 34 deforming or otherwise "digging into" the inner surface of sheath 16. This may increase the amount of force required to pull back sheath 16 and deploy stent 34. Reinforcing member 42 may help to reduce deformation along the inner surface of sheath 16, thereby reducing the deployment forces. For example, FIG. 7 schematically illustrates a force F (e.g., a radially outward force being exerted by stent 34) being applied to sheath 16. Reinforcing member 42 may reduce the amount of deformation along sheath 16. For example, the force F may cause little or no deformation of sheath 16 and, in FIG. 7, is schematically shown as a deformation/deflection of a distance D1. For example, when an axial stress of about 5-10 lbs or about 8 lbs of force is applied, strain may be kept at about 0.1 to 0.2 inches or less, or about 0.1 inches or less. In contrast, a sheath 116 including inner liner 150 and outer layer 152 (e.g., as shown in FIG. 8) but lacking reinforcing member 42, may be subjected to addition deformation/deflection of a distance D2, where D2 would be larger than D1, increasing the "digging in" of the stent 34 to the inner surface of the sheath 116, thereby increasing the force required to pull back the sheath 116 to deploy stent 34.

Without wishing to be bound by theory, when stent 34 applies outward pressure onto a structure constraining it (e.g., sheath 16 or sheath 116), assuming similar dimensions, the structure that includes materials with a larger elastic modulus or hardness (e.g., sheath 16 including reinforcing member 42) may be more resistance to stent movement or "creep" over time. In addition, stent 34 should also "dig in" less. Collectively, these features may reduce deployment forces. In addition, reinforcing member 42 may also reduce or otherwise limit axial strain, which may also reduce transverse strain (e.g., based on the material's property for Poisson's Ratio), thereby reducing the pressure/force between stent 34 and sheath 16. Axial strain could result in the inner diameter of sheath 16 reducing. Therefore, reducing axial strain also helps to reduce deployment force by reducing axial strain-related decreases in inner diameter.

In some instances, reinforcing member 42 may include other structural variations. For example, in embodiments where reinforcing member 42 includes a braid, the pic count may vary. In some instances, reinforcing member 42 may have a "relatively high" pic count (e.g., about 90-150 pics per inch) to add flexibility and reduce kinks around a tight radius. In some instances, reinforcing member 42 may have a lower pic count (e.g., about 40-72 pics per inch) to increase pushability/torqueability to outer sheath 16. Other variations are contemplated.

Figure 9:
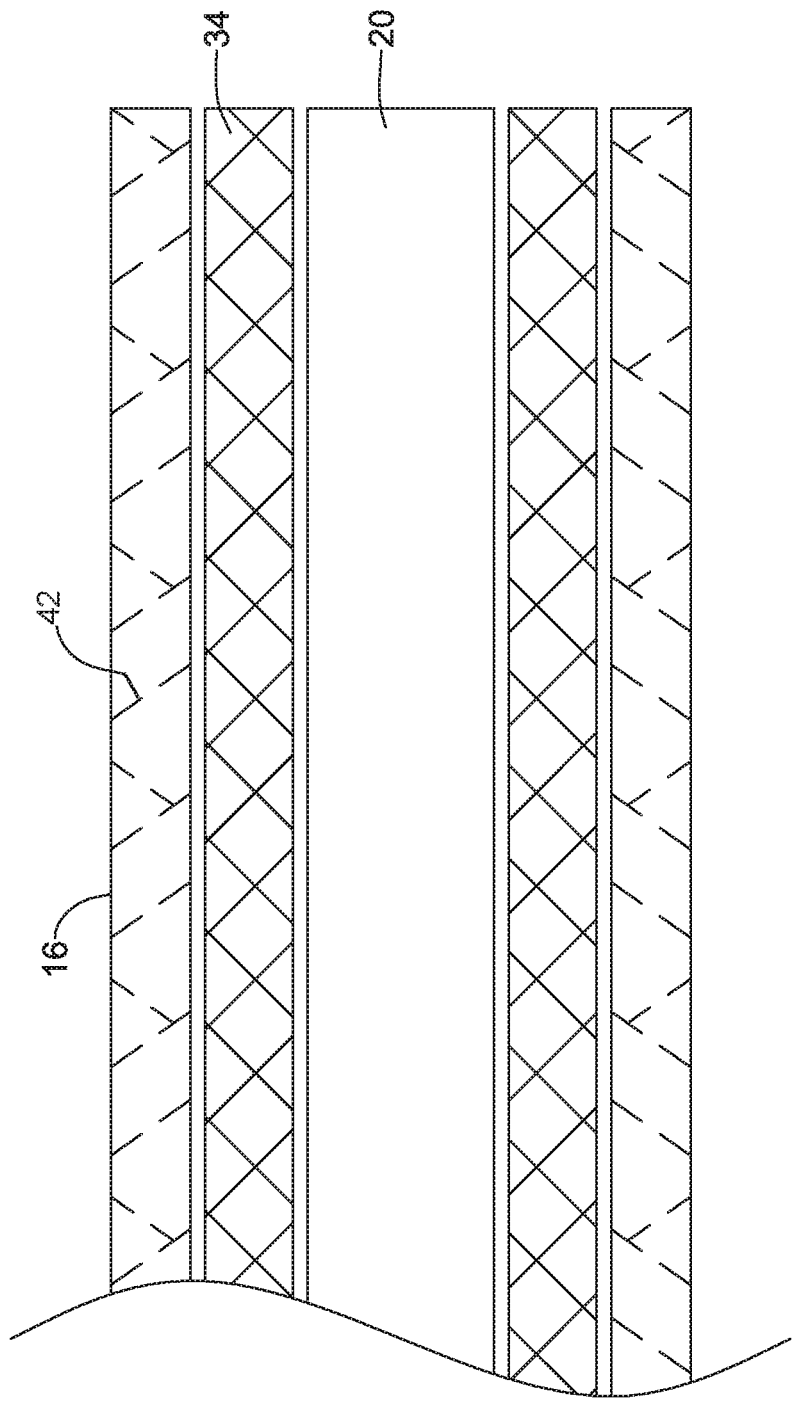
FIG. 9 is a partial cross-sectional side view of a portion of the example stent delivery system.

FIG. 9 illustrates sheath 16 positioned over stent 34 and inner member 20. Again, reinforcing member 42 is shown in phantom line to schematically illustrate that stent 34 can be visualized through reinforcing member 42 (and/or sheath 16). In some instances, system 10 may be used along the biliary tract, enteral tract, an airway, or the like. Such interventions may include the use of a visualization device such as an endoscopic visualization device. The use of translucent reinforcing member 42 may allow for the endoscopic visualization device to directly visualize stent 34 within sheath 16, for example, before and/or during deployment.

Manufacturing sheath 16 may include a number of steps. For example, manufacturing sheath 16 may include disposing inner liner 50 along a mandrel. In some instances, liner 50 may be stretched and secured at its ends to the mandrel. Reinforcing member 42 may be disposed over liner 50. This may include disposing reinforcing member 42 over one or more discrete portions of liner 50 (e.g., a distal portion) or along the full length of liner 50. When reinforcing member 42 takes the form of a braid, reinforcement may be braided in a braid pattern that has about 52-90 pic/inch. In some instances, an additional reinforcement (not shown) may be disposed over the proximal section of liner 50 (e.g., which may include disposing the additional reinforcement over the proximal portion of reinforcing member 42). The additional reinforcement may take the form of a metallic braid (e.g., stainless steel or other suitable materials). Outer layer 52 may be disposed over liner 50 and reinforcing member 42 (and the additional reinforcement, if present). In some instances, a radiopaque marker band may be disposed over a portion of liner 50 prior to the addition of outer layer 52. A heat shrink material (e.g., fluorinated ethylene propylene) may be disposed over the entire assembly and heat may be added to reflow/laminate adjacent tubes/layers together. When doing so, reinforcing member 42 may be encapsulated and outer layer 52 may be mechanically bonded to liner 50. Any excess portion of liner 50 may be skived off and the resultant structure may be trimmed to the desired length and removed from the mandrel. The manufacturing of system may include manufacturing sheath 16, disposing inner member 20 within sheath 16, and disposing stent 34 between sheath 16 and inner member 20.

The materials that can be used for the various components of system 10 (and/or other systems disclosed herein) may include those commonly associated with medical devices. For simplicity purposes, the following discussion makes reference to shaft 12, deployment sheath 16, and inner member 20. However, this is not intended to limit the invention as the discussion may be applied to other similar members and/or components of members or systems disclosed herein.

Shaft 12, deployment sheath 16, and inner member 20, and/or other components of system 10 may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau"

or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of shaft 12, deployment sheath 16, and inner member 20 may also be doped with, made of, or otherwise include a radiopaque material including those listed herein or other suitable radiopaque materials.

In some embodiments, a degree of Mill compatibility is imparted into system 10. For example, to enhance compatibility with Magnetic Resonance Imaging (Mill) machines, it may be desirable to make shaft 12, deployment sheath 16, and inner member 20, in a manner that would impart a degree of MRI compatibility. For example, shaft 12, deployment sheath 16, and inner member 20, or portions thereof, may be made of a material that does not substantially distort the image and create substantial artifacts (artifacts are gaps in the image). Certain ferromagnetic materials, for example, may not be suitable because they may create artifacts in an Mill image. Shaft 12, deployment sheath 16, and inner member 20, or portions thereof, may also be made from a material that the Mill machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be used to form shaft 12, deployment sheath 16, and inner member 20, and/or other components of system 10 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® and/or GRILAMID® TR55-LX available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the exterior surface of the system 10 may include a coating, for example a lubricious, a hydrophilic, a protective, or other type of coating. Hydrophobic coatings such as fluoropolymers provide a dry lubricity which improves device handling and exchanges. Lubricious coatings improve steerability and improve lesion crossing capability. Suitable lubricious polymers may include silicone and the like, polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference.

U.S. Pat. Nos. 9,084,692 and 8,784,468 as well as U.S. Patent Application Pub. No. US 2013/0013047 are incorporated herein.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A stent delivery system, comprising:
   an inner member;
   a deployment sheath disposed about the inner member, wherein at least a distal region of the deployment sheath is translucent;
   a stent disposed between the inner member and the deployment sheath; and
   a translucent reinforcing member disposed within the translucent distal region of the deployment sheath, wherein the translucent reinforcing member and the translucent distal region of the deployment sheath allow for visualization of the stent during stent deployment.

2. The stent delivery system of claim 1, wherein the stent includes a self-expanding stent.

3. The stent delivery system of claim 1, wherein the translucent reinforcing member includes a braid.

4. The stent delivery system of claim 1, wherein the translucent reinforcing member includes a coil.

5. The stent delivery system of claim 1, wherein the translucent reinforcing member includes a polymer.

6. The stent delivery system of claim 1, wherein the translucent reinforcing member includes polyetheretherketone.

7. The stent delivery system of claim 1, wherein the deployment sheath extends from a proximal end of the deployment sheath to a distal end of the deployment sheath.

8. The stent delivery system of claim 1, wherein the deployment sheath has a proximal region, and wherein the translucent reinforcing member extends along the translucent distal region.

9. The stent delivery system of claim 8, wherein the translucent distal region has an enlarged outer diameter relative to the proximal region, an enlarged inner diameter relative to the proximal region, or both.

10. The stent delivery system of claim 1, wherein the deployment sheath includes an inner liner and an outer layer, and wherein at least a portion of the translucent reinforcing member is disposed between the inner liner and the outer layer.

11. The stent delivery system of claim 10, wherein the inner liner, the outer layer, or both are at least partially translucent.

12. The stent delivery system of claim 1, further comprising a handle coupled to the inner member and to the deployment sheath, the handle including an actuation member capable of translating the deployment sheath relative to the inner member.

13. A stent delivery system for use along a biliary tract, an enteral tract, or an airway, the stent delivery system comprising:
    an inner member;
    a deployment sheath disposed about the inner member;
    a self-expanding stent disposed between the inner member and the deployment sheath; and
    wherein the deployment sheath includes an inner liner, an outer layer, and a translucent braided reinforcing member disposed at least partially between the inner liner and the outer layer;
    wherein the inner liner and the outer layer are translucent; and
    wherein the inner liner, the outer layer, and the translucent braided reinforcing member allow for visualization of the self-expanding stent during stent deployment.

14. The stent delivery system of claim 13, wherein the translucent braided reinforcing member includes a polymer.

15. The stent delivery system of claim 13, wherein the translucent braided reinforcing member includes polyetheretherketone.

16. The stent delivery system of claim 13, wherein the deployment sheath has a proximal region and a distal region, and wherein the translucent braided reinforcing member extends along at least the distal region.

17. The stent delivery system of claim 16, wherein the distal region has an enlarged outer diameter relative to the proximal region, an enlarged inner diameter relative to the proximal region, or both.

\* \* \* \* \*